US007488535B2

(12) United States Patent
Ehrnsperger et al.

(10) Patent No.: US 7,488,535 B2
(45) Date of Patent: Feb. 10, 2009

(54) ABSORBENT CORES FOR ABSORBENT DIAPERS HAVING REDUCED THICKNESS AND IMPROVED LIQUID HANDLING AND RETENTION PERFORMANCE AND COMPRISING A SUPER ABSORBENT POLYMER

(75) Inventors: Bruno Johannes Ehrnsperger, Evendale, OH (US); Udo Friedel Schoenborn, Bad Soden (DE)

(73) Assignee: The Procter & Gamble Company, Cincinnati, OH (US)

( * ) Notice: Subject to any disclaimer, the term of this patent is extended or adjusted under 35 U.S.C. 154(b) by 144 days.

(21) Appl. No.: 11/704,851

(22) Filed: Feb. 9, 2007

(65) Prior Publication Data

US 2007/0134492 A1 Jun. 14, 2007

Related U.S. Application Data

(63) Continuation of application No. 10/645,362, filed on Aug. 21, 2003, now Pat. No. 7,175,910.

(30) Foreign Application Priority Data

Aug. 26, 2002 (EP) .................................. 02078518

(51) Int. Cl.
*B32B 5/16* (2006.01)
(52) U.S. Cl. .................. 428/403; 428/404; 428/405; 428/406; 428/407; 428/304.4; 428/284; 521/138; 521/149; 604/367; 604/368; 604/378
(58) Field of Classification Search .................. 428/403, 428/404, 405, 406, 407, 304.4, 284; 521/138, 521/149; 604/367, 368, 378
See application file for complete search history.

(56) References Cited

U.S. PATENT DOCUMENTS

| 3,699,103 | A | 10/1972 | Kiss |
| 3,770,731 | A | 11/1973 | Jaeger |
| 4,020,780 | A | 5/1977 | Shumaker et al. |
| 4,076,663 | A | 2/1978 | Masuda et al. |
| 4,340,706 | A | 7/1982 | Obayashi et al. |
| 4,421,602 | A | 12/1983 | Brunnmueller et al. |
| 4,506,052 | A | 3/1985 | Furukawa et al. |
| 4,541,871 | A | 9/1985 | Obayashi et al. |
| 4,587,308 | A | 5/1986 | Makita et al. |
| 4,625,001 | A | 11/1986 | Tsubakimoto et al. |
| 4,654,039 | A | 3/1987 | Brandt et al. |
| 4,666,983 | A | 5/1987 | Tsubakimoto et al. |
| 4,673,402 | A | 6/1987 | Weisman et al. |
| 4,734,478 | A | 3/1988 | Tsubakimoto et al. |
| RE32,649 | E | 4/1988 | Brandt et al. |
| 4,735,987 | A | 4/1988 | Morita et al. |
| 4,789,861 | A | 12/1988 | Baggett et al. |
| 4,824,901 | A | 4/1989 | Alexander et al. |
| 4,834,735 | A | 5/1989 | Alemany et al. |
| 4,935,022 | A | 6/1990 | Lash et al. |
| 5,047,023 | A | 9/1991 | Berg |
| 5,061,259 | A | 10/1991 | Goldman et al. |
| 5,124,188 | A | 6/1992 | Roe et al. |
| 5,147,343 | A | 9/1992 | Kellenberger |
| 5,147,345 | A | 9/1992 | Young et al. |
| 5,149,335 | A | 9/1992 | Kellenberger et al. |
| 5,164,459 | A | 11/1992 | Kimura et al. |
| 5,217,445 | A | 6/1993 | Young et al. |
| 5,374,684 | A | 12/1994 | Tai |

(Continued)

FOREIGN PATENT DOCUMENTS

WO    WO 92/16565 A1    10/1992

(Continued)

*Primary Examiner*—Leszek Kiliman
(74) *Attorney, Agent, or Firm*—John G. Powell

(57) ABSTRACT

The present invention relates to absorbent cores for absorbent articles, which are intended to receive and retain bodily discharges such as urine. Such articles are disposable hygiene articles like baby diapers, training pants, adult incontinence articles, feminine care articles and the like. The improvement essentially is based on the recognition that replacing most or all of the cushioning fibrous absorbent material in an absorbent core by a liquid storage material capable of retaining liquid while maintaining or improving acquisition behavior is desirable as the reduction in cushioning is more than compensated by the gain in comfort. The comfort however can only be achieved if the more fundamental requirements of a diaper in respect to liquid handling are satisfied or improved. Especially if this liquid handling performance is improved beyond the performance of conventional absorbent structures in order to allow creation of thinner and drier absorbent articles, the users of such articles would experience them as providing a more than expected comfort improvement relative to the thinness gain. To provide such absorbent cores and articles made therewith only became possible with the development of new highly absorbent gel materials capable of acquiring, conducting, and storing liquids in here-to-fore unexpected perfection at super absorbent polymer concentrations, which are unknown today. The second aspect allowing this breakthrough development is the ability to maintain the comfort and performance of such high super absorbent polymer concentration articles during the full usage cycle of the article, from dry to fully loaded, especially by improving the ability of the cores to withstand the forces experienced by such articles during use. This ability to remain intact is also often referred to as wet integrity of the core and its improvement is an important objective of the present invention.

18 Claims, No Drawings

U.S. PATENT DOCUMENTS

| | | | |
|---|---|---|---|
| 5,382,610 A | 1/1995 | Harada et al. | |
| 5,509,915 A | 4/1996 | Hanson et al. | |
| 5,562,646 A | 10/1996 | Goldman et al. | |
| 5,633,316 A | 5/1997 | Gartner et al. | |
| 5,669,894 A | 9/1997 | Goldman et al. | |
| 5,744,564 A | 4/1998 | Stanley, Jr. et al. | |
| 5,843,575 A | 12/1998 | Wang et al. | |
| 5,849,405 A * | 12/1998 | Wang et al. | 428/304.4 |
| 5,851,672 A * | 12/1998 | Wang et al. | 428/407 |
| 5,985,432 A * | 11/1999 | Wang et al. | 428/304.4 |
| 6,121,509 A | 9/2000 | Ashraf et al. | |
| 6,342,298 B1 | 1/2002 | Evans et al. | |
| 6,730,387 B2 | 5/2004 | Rezai et al. | |
| 6,832,905 B2 * | 12/2004 | Delzer et al. | 425/80.1 |

FOREIGN PATENT DOCUMENTS

| | | |
|---|---|---|
| WO | WO 93/05080 A1 | 3/1993 |

* cited by examiner

ABSORBENT CORES FOR ABSORBENT DIAPERS HAVING REDUCED THICKNESS AND IMPROVED LIQUID HANDLING AND RETENTION PERFORMANCE AND COMPRISING A SUPER ABSORBENT POLYMER

CROSS REFERENCE TO RELATED APPLICATIONS

This application is a continuation of Ser. No. 10/645,362, filed Aug. 21, 2003.

FIELD OF THE INVENTION

The present invention relates to absorbent cores for absorbent articles, which are intended to receive and retain bodily discharges such as urine. Such articles are disposable hygiene articles like baby diapers, training pants, adult incontinence articles, feminine care articles and the like. The improvement essentially is based on the recognition that replacing most or all of the cushioning fibrous absorbent material in an absorbent core by a liquid storage material capable of retaining liquid while maintaining or improving acquisition behavior is desirable as the reduction in cushioning is more than compensated by the gain in comfort. The comfort however can only be achieved if the more fundamental requirements of a diaper in respect to liquid handling are satisfied or improved. Especially if this liquid handling performance is improved beyond the performance of conventional absorbent structures in order to allow creation of thinner and drier absorbent articles, the users of such articles would experience them as providing a more than expected comfort improvement relative to the thinness gain. To provide such absorbent cores and articles made therewith only became possible with the development of new highly absorbent gel materials able to acquire, conduct, and store liquids in here-to-fore unexpected perfection at super absorbent polymer concentrations, which are unknown today. The second aspect allowing this breakthrough development is the ability to maintain the comfort and performance of such high super absorbent polymer concentration articles during the full usage cycle of the article, from dry to fully loaded, especially by improving the ability of the cores to withstand the forces experienced by such articles during use. This ability to remain intact is also often referred to as wet integrity of the core and its improvement is an important objective of the present invention.

BACKGROUND OF THE INVENTION

Absorbent articles for receiving and retaining bodily discharges such as urine or faeces such as disposable diapers, training pants, and adult incontinence articles are well known in the art, and significant effort has been spent against improving their performance. Such improvements generally aim at addressing the primary function of such articles, namely retaining body fluids, but also at minimizing the negatives associated with wearing such articles by increasing the comfort of the wearer.

Such improvements can mostly be classified to primarily fall within either of two categories: primarily relating to "core technology", i.e., "absorbency" in the broad sense of the word, or primarily relating to "chassis technology".

The first addresses how to pick up and retain the body waste (generally in some state of fluidity) in an "absorbent (or core) structure", whereby the waste material is acquired by the article (picked up), then conducted away from the location of acquisition (distribution), and then stored (retained).

The second category deals—generally—with the so called "chassis elements" to contain the body waste within the confinement of the article. This can be done by separating the absorbent (core) structure and the outside, e.g., wearers' garments or skin, by using an impermeable backsheet. Additionally the chassis should prevent bodily exudates from escaping through the space between the absorbent article and the body of the wearer, which can be achieved by elasticized gatherings at leg and waist openings. Other chassis aspects enable application of the article to the wearer—e.g., by providing closure means such as tapes, or maintain the article on the wearer by belt like arrangements (integral with the article in so called pull-up diaper designs or as part of the application means).

Often the terminology "comfort" for the wearer was predominantly addressed by improving chassis elements, such as by adopting the chassis elements of the diaper to provide good "fit" of the article and to be soft and cushioning. It is also well established that reducing the thickness of the article by reducing the primary thickness cause, i.e., the absorbent (core) structure helps to improve comfort. This however was always a question of balance between liquid handling performance and thickness. Also a substantial amount of cushioning was considered necessary for comfortable diapers. Finally, the skilled person considered it impossible to reduce or even remove the fibrous material to a point where the modern particulate super absorbent materials would take over part or all of the liquid acquisition and distribution functionalities previously provided by fibrous matrixes. Finally, even if there were structures which could possibly provide all such beneficial aspects when dry, it was completely in-conceivable that this could be build into an absorbent (core) structure such that the liquid handling and comfort performance would be maintained even after the first gushes of liquid had been absorbed.

The development of absorbent (core) structures of particular thinness has also other beneficial aspects making such a development the subject of substantial commercial interest. For example, thinner diapers are not just less bulky to wear and fit better under clothing they are also more compact in the package, making the diapers easier for the consumer to carry and store. Compactness in packaging also results in reduced distribution costs for the manufacturer and distributor, including less shelf space required in the store per diaper unit.

As indicated, the ability to provide thinner absorbent articles such as diapers has been contingent on the ability to develop relatively thin absorbent (core) structures that can acquire and store large quantities of discharged body fluids, in particular urine. In this regard, the use of absorbent polymers often referred to as "hydrogels," "super absorbents" or "hydrocolloid" material has been particularly important. See, for example, U.S. Pat. No. 3,699,103 (Harper et al), issued Jun. 13, 1972, and U.S. Pat. No. 3,770,731 (Harmon), issued Jun. 20, 1972, that disclose the use of such absorbent polymers (hereafter referred to as any of the following: hydrogel forming absorbent polymers, super absorbents, super absorbent polymers or SAPs, absorbent gel materials or AGMs). Indeed, the development of thinner diapers has been the direct consequence of thinner absorbent cores that take advantage of the ability of these SAPs to absorb large quantities of discharged body fluids, typically when used in combination with a fibrous matrix. See, for example, U.S. Pat. No. 4,673,402 (Weisman et al), issued Jun. 16, 1987 and U.S. Pat. No. 4,935,022 (Lash et al), issued Jun. 19, 1990, that disclose dual-layer core structures comprising a fibrous matrix and SAPs useful in fashioning thin, compact, non-bulky diapers.

Prior to the use of these SAPs, it was general practice to form absorbent structures, such as those suitable for use in infant diapers, entirely from wood pulp fluff. Given the relatively low amount of fluid absorbed by wood pulp fluff on a gram of fluid absorbed per gram of wood pulp fluff, it was necessary to employ relatively large quantities of wood pulp fluff, thus necessitating the use of relatively bulky, thick absorbent structures. The introduction of these SAPs into such structures has allowed the use of less wood pulp fluff. These SAPs are superior to fluff in their ability to absorb large volumes of aqueous body fluids, such as urine (i.e., at least about 15 g/g), thus making smaller, thinner absorbent structures feasible. In addition SAP particles typically pack closer than fibrous structures, thus achieving even thinner cores at elevated concentrations.

These SAPs are often made by initially polymerizing unsaturated carboxylic acids or derivatives thereof, such as acrylic acid, alkali metal (e.g., sodium and/or potassium) or ammonium salts of acrylic acid, alkyl acrylates, and the like. These polymers are rendered water-insoluble, yet water-swellable, by slightly cross-linking the carboxyl group-containing polymer chains with conventional di- or poly-functional monomer materials, such as N,N'-methylene-bisacrylamide, trimethylol-propane-triacrylate or triallyl-amine. These slightly cross-linked absorbent polymers still comprise a multiplicity of anionic (charged) carboxyl groups attached to the polymer backbone. It is these charged carboxyl groups that enable the polymer to absorb body fluids as the result of osmotic forces, thus forming hydrogels.

The degree of cross-linking determines not only the water-insolubility of these SAPs, but is also an important factor in establishing two other characteristics of these polymers: their absorbent capacity and gel strength. Absorbent capacity or "gel volume" is a measure of the amount of water or body fluid that a given amount of SAP will absorb. Gel strength relates to the tendency of the SAP to deform or "flow" under an applied stress. SAPs useful as absorbents in absorbent structures and articles such as disposable diapers need to have adequately high gel volume, as well as adequately high gel strength. Gel volume needs to be sufficiently high to enable the SAP to absorb significant amounts of the aqueous body fluids encountered during use of the absorbent article. Gel strength needs to be such that the SAP formed does not deform and fill to an unacceptable degree the capillary void spaces in the absorbent structure or article, thereby inhibiting the absorbent capacity of the structure/article, as well as the fluid distribution throughout the structure/article. See, for example, U.S. Pat. No. 4,654,039 (Brandt et al), issued Mar. 31, 1987 (reissued Apr. 19, 1988 as U.S. Reissue Pat. 32,649) and U.S. Pat. No. 4,834,735 (Alemany et al), issued May 30, 1989.

Prior absorbent structures have generally comprised relatively low amounts (e.g., less than about 50% by weight) of these SAPs. See, for example, U.S. Pat. No. 4,834,735 (Alemany et al.), issued May 30, 1989 (preferably from about 9 to about 50% SAP in the fibrous matrix). There are several reasons for this. The SAPs employed in prior absorbent structures have generally not had an absorption rate that would allow them to quickly absorb body fluids, especially in "gush" situations. This has necessitated the inclusion of fibers, typically wood pulp fibers, to serve as temporary reservoirs to hold the discharged fluids until absorbed by the SAP.

More importantly, many of the known SAPs exhibited gel blocking. "Gel blocking" occurs when particles of the SAP are wetted and the particles swell so as to inhibit fluid transmission to other regions of the absorbent structure. Wetting of these other regions of the absorbent member therefore takes place via a very slow diffusion process. In practical terms, this means acquisition of fluids by the absorbent structure is much slower than the rate at which fluids are discharged, especially in gush situations. Leakage from the absorbent article can take place well before the particles of SAP in the absorbent member are even close to being fully saturated or before the fluid can diffuse or wick past the "blocking" particles into the rest of the absorbent member. Gel blocking can be a particularly acute problem if the particles of SAP do not have adequate gel strength and deform or spread under stress once the particles swell with absorbed fluid. See U.S. Pat. No. 4,834,735 (Alemany et al), issued May 30, 1989.

This gel blocking phenomena has typically necessitated the use of a fibrous matrix in which are dispersed the particles of SAP. This fibrous matrix keeps the particles of SAP separated from one another. This fibrous matrix also provides a capillary structure that allows fluid to reach the SAP located in regions remote from the initial fluid discharge point. See U.S. Pat. No. 4,834,735 (Alemany et al), issued May 30, 1989. However, dispersing the SAP in a fibrous matrix at relatively low concentrations in order to minimize or avoid gel blocking can lower the overall fluid storage capacity of thinner absorbent structures. Usage of lower concentrations of these SAPs limits somewhat the real advantage of these materials, namely their ability to absorb and retain large quantities of body fluids per given volume. Another reason why extremely high concentrations of SAP were not possible resides in the physical integrity disadvantage of structures made of particulate material. Creating a fibrous matrix therefore also had the advantage of providing a fiber re-enforced structure, similar to those used in many other technical situations where structural re-enforcement is provided by fibrous elements, such as in fiberglass.

Besides increasing gel strength, other physical and chemical characteristics of these SAPs have been manipulated to improve their performance especially to decrease gel blocking. One characteristic is the particle size, and especially the particle size distribution. In this context it should be mentioned that the present invention relates to absorbent cores comprising particulate SAPs. The use of fibrous SAPs does eliminate many of the problems found with particulate SAPs, but raises different issues. One key problem, which so far has typically led away from commercial usage of fibrous SAP (i.e., regardless of technical aspects), is the cost differential between SAP particles and SAP fibers. According to U.S. Pat. No. 5,047,023 (Berg), issued Sep. 10, 1991 the particle size distribution of the SAP can be controlled to improve absorbent capacity and efficiency of the particles employed in the absorbent structure. However, even adjusting the particle size distribution does not, by itself, lead to absorbent structures that can have relatively high concentrations of these SAPs. Another characteristic of these SAPs that has been looked at is the level of extractables present in the polymer itself; see e.g., U.S. Reissue Pat. 32,649 (Brandt et al.), reissued Apr. 19, 1988.

Yet another characteristic the art has known for some time, as a measure of gel blocking is the Demand Wettability or Gravimetric Absorbence of these SAPs. See, for example, U.S. Pat. No. 5,147,343 (Kellenberger), issued Sep. 15, 1992 and U.S. Pat. No. 5,149,335 (Kellenberger et al.), issued Sep. 22, 1992 where these SAPs are referred to as "superabsorbent materials" and where Demand Wettability/Gravimetric Absorbence is referred to as Absorbency Under Load (AUL). "AUL" is defined in these patents as the ability of the SAP to swell against an applied restraining force (see U.S. Pat. No. 5,147,343, supra, at Col. 2, lines 43-46). The "AUL value" is defined as the amount (in ml./g or g/g.) of 0.9% saline solution that is absorbed by the SAPs while being subjected to a load of 21,000 dynes/cm2 (about 0.3 psi). The AUL value can be determined at 1 hour (see U.S. Pat. No. 5,147,343) or 5 minutes (see U.S. Pat. No. 5,149,335). SAPs are deemed to have desirable AUL properties if they absorb at least about 24 ml./g (preferably at least about 27 ml./g) of the saline solution after 1 hour (see U.S. Pat. No. 5,147,343) or at least about 15 g/g (preferably at least about 18 g/g) of the saline solution after 5 minutes.

AUL as defined in U.S. Pat. Nos. 5,147,343 and 5,149,335 may provide some indication of which SAPs will avoid gel blocking in some instances. However, AUL is inadequate for determining which SAPs will provide the absorbency properties necessary so that the concentration of these polymers in absorbent structures can be increased without significant gel blocking or some other undesirable effect. Indeed, certain of the SAPs disclosed in U.S. Pat. Nos. 5,147,343 and 5,149,335 as having satisfactory AUL values will have inadequate permeability to be useful at high concentrations in absorbent members. In order to have a high AUL value, it is only necessary that the hydrogel layer formed have at least minimal permeability such that, under a confining pressure of 0.3 psi, gel blocking does not occur to any significant degree. The degree of permeability needed to simply avoid gel blocking is much less than that needed to provide good fluid transportation properties. SAPs that avoid gel blocking by AUL selection according to U.S. Pat. Nos. 5,147,343 and 5,149,335 can still be greatly deficient in other fluid handling properties.

Another problem with using AUL values measured according to U.S. Pat. Nos. 5,147,343 and 5,149,335 is that they do not reflect all of the potential pressures that can be operative on the hydrogel-forming polymer in the absorbent structure. As noted above, AUL is measured in these patents at a pressure of about 0.3 psi. It is believed that a much higher confining pressure of about 0.7 psi. more adequately reflects the full range of localized mechanical pressures (e.g., sitting, sleeping, squatting, taping, elastics, leg motions, other tension and torsion motions) on an absorbent structure. See U.S. Pat. No. 5,147,345 (Young et al.), issued Sep. 15, 1992. Additionally, many of the absorbent structures that comprise these SAPs can include other components, such as an acquisition layer that receives the initial discharge of body fluids. See, for example, U.S. Pat. No. 4,673,402 (Weisman et al.), issued Jun. 16, 1987 and U.S. Pat. No. 4,935,022 (Lash et al.), issued Jun. 19, 1990. This acquisition layer can comprise fibers, such as certain chemically stiffened fibers, that have a relatively high capillary suction. See, for example, U.S. Pat. No. 5,217,445 (Young et al.), issued Jun. 8, 1993. To take into account these additional capillary pressures that could affect fluid acquisition by these SAPs, it is more realistic to measure demand absorbency performance under a higher pressure, i.e., approximately 0.7 psi. This would take into better account not only the localized mechanical pressures exerted during use, but also the additional capillary pressures resulting from other components (e.g., acquisition layer) present in the absorbent structure.

For absorbent structures having relatively high concentrations of these SAPs, other characteristics of these absorbent polymers have been evaluated. See, for example, European patent application 532,002 (Byerly et al.), published Mar. 17, 1993, which identifies a characteristic called Deformation Under Load (DUL) as being important for absorbent composites having high concentrations of SAPs. "DUL" is used in European patent application 532,002 to evaluate the ability of the SAP to maintain wicking channels after the absorbent polymer is swollen. See page 3, lines 9-10. DUL values are obtained by incompletely saturating the SAP with a fixed amount of synthetic urine, compressing the absorbent polymer under a light load (0.3 psi), and then measuring the deformation of the absorbent polymer under a heavier load (0.9 psi). In this application SAPs having DUL values of about 0.6 mm or less are disclosed.

DUL as defined in European patent application 532,002 may provide some indication of the ability of SAP to maintain wicking channels after the absorbent polymer is swollen. However, it has been found that the openness or porosity of the hydrogel layer, hereinafter referred to as PHL (for a further definition see PCT WO-95-26209, page 17 following or EP-B-752892 paragraph 64 following), which is formed when these absorbent polymers swell in the presence of body fluids is more relevant than DUL values for determining the ability of these absorbent polymers to acquire and transport fluids, especially when the absorbent polymer is present at high concentrations in the absorbent structure. Porosity refers to the fractional volume that is not occupied by solid material. For a hydrogel layer formed entirely from a SAP, porosity is the fractional volume of the layer that is not occupied by hydrogel. For an absorbent structure containing the hydrogel, as well as other components, porosity is the fractional volume (also referred to as void volume) that is not occupied by the hydrogel, or other solid components (e.g., fibers).

Importantly, it has been found that SAPs having higher porosities than those apparently desired by European patent application 532,002 are particularly suitable for absorbent structures having high concentrations of these absorbent polymers. It is believed that the SAPs having DUL values below about 0.6 mm that are desired by European patent application 532,002 have relatively low porosities.

Another important property at higher concentrations of these SAPs is their permeability/flow conductivity. Permeability/flow conductivity can be defined in terms of their Saline Flow Conductivity (SFC) values. SFC is well established in the art and defined in great detail e.g., in PCT WO-95-26209, page 69 following or EP-B-752892 paragraph 224 following. SFC measures the ability of a material to transport saline fluids, such as the ability of the hydrogel layer formed from the swollen SAP to transport body fluids. Typically, an air-laid web of pulp fibers (e.g., having a density of 0.15 g/cc) will exhibit an SFC value of about 200×10-7 $cm^3sec/g$. By contrast, typical SAPs such as Aqualic L-74 (made by Nippon Shokubai Co., LTD) and Nalco-1180 (made by Nalco Chemical Co.) exhibit SFC values of at most 1×10-7 $cm^3sec/g$. Accordingly, it would be highly desirable to be able to use SAPs that more closely approach an air-laid web of wood pulp fibers in terms of SFC.

Another factor that has to be considered in order to take full advantage of the porosity and permeability properties of the hydrogel layer formed from these SAPs is the wet integrity of the region or regions in the absorbent member that comprise these polymers. For SAPs having relatively high porosity and SFC values, it is extremely important that the region(s) in which polymers are present have good wet integrity. By "good wet integrity" is meant that the region or regions in the absorbent member having the high concentration of SAP have sufficient integrity in a dry, partially wet, and/or wetted state such that the physical continuity (and thus the capability of acquiring and transporting fluid through contiguous interstitial voids/capillaries) of the hydrogel formed upon swelling in the presence of body fluids is not substantially disrupted or altered, even when subjected to normal use conditions. During normal use, absorbent cores in absorbent articles are typically subjected to tensional and torsion forces of varying intensity and direction. These tensional and torsion forces include bunching in the crotch area, stretching and twisting forces as the person wearing the absorbent article walks, squats, bends, and the like. If wet integrity is inadequate, these tensional and torsion forces can potentially cause a substantial alteration and/or disruption in the physical continuity of the hydrogel such that its capability of acquiring and transporting fluids into and through the contiguous voids and capillaries is degraded, e.g., the hydrogel layer can be partially separated, fully separated, have gaps introduced, have areas that are significantly thinned, and/or broken up into a plurality of significantly smaller segments. Besides the macroscopic discomfort such lack of integrity inevitably creates it can also minimize or completely negate any advantageous porosity and permeability/flow conductivity properties of the SAP. In order to evaluate the behavior of a hydrogel layer a so-called ball burst evaluation can be made allowing predicting or drawing conclusions about the expected behavior within certain limits of the absorbent article in use. In particular the test allows evaluating the relative deterioration of the wet integrity of absorbent cores comprising a high SAP concentration Accordingly, it would be desirable to be able to provide an absorbent member comprising: (1) a region or regions having a relatively high concentration of SAP particles; (2) with relatively high porosities, and preferably permeability/flow conductivity properties more like an air-laid fibrous web; (3) that can readily acquire fluids from even high capillary suction acquisition layers under typical usage pressures; (4) in a matrix that provides sufficient wet integrity such that its capability for acquiring and transporting fluids is not substantially reduced or minimized, even when subjected to normal use forces. It would also be highly desirable to be able to use SAPs in these absorbent members that, when swollen by body fluids, continue to have a good wet integrity and high porosity such that: (a) the void volume per unit weight of absorbent polymer is closer to that of an air-laid fibrous web; (b) the demand wet ability or gravimetric absorbency of the absorbent polymer under usage pressures is increased; and (c) the absorbent polymer preferably has increased permeability, improved wicking and/or improved swelling properties.

Hence it is an object of the present invention to provide absorbent articles having an improved fit especially by reducing their thickness but also when being loaded, together with good fluid handling performance, especially by using materials having particularly suitable fluid distribution properties when dry and during progressive saturation with liquids.

It is a further object of the invention to achieve this by using Super absorbent polymers.

SUMMARY OF THE INVENTION

The present invention and its characteristics are fully defined in the independent claims and preferred embodiments are specified in the dependant claims. In particular the present invention relates to absorbent cores useful in the provision of absorbent incontinence articles such as baby diapers or adult incontinence articles, which articles preferably comprise a topsheet with the absorbent core positioned immediately adjacent to it and further optionally a backsheet which together with the topsheet sandwiches the absorbent core.

The absorbent cores of the present invention are especially useful for collection of bodily liquids such as urine. Such cores comprise super absorbent gelling material, which is in the form of particles. The particles, in contrast to fibers, have a longest and a smallest dimension with a particulate ratio of longest to smallest particle dimension in the range of 1-5, where a value of 1 would equate a perfectly spherical particle and 5 would allow for some deviation from such a spherical particle.

The particles are provided with a surface cross-linking in order to provide individual particle stability such that super absorbent gelling material has a measured SFC value of at least 30 units in accordance with the SFC test as defined herein, preferably more than 60 units.

The particles further have a substantially non-covalently bonded surface coating with a partially hydrolysable cationic polymer, such that said super absorbent gelling material has a measured ball burst strength (hereinafter referred to as BBS) of more than 80 grams of force after 30 minutes and a BBS after 16 hours of at least 50% of the BBS after 30 minutes in accordance with the BBS test as defined herein. Preferably the BBS is 100 to 130 grams of force after 30 minutes and BBS after 16 hours is in the range of 80%-120% of the BBS after 30 minutes. In order to fine-tune (stabilize or buffer) the cationic charge on the polymer it should be a hydrolysable polymer.

The covalent coating is present on the particles in an amount of less than 10% by weight of said particles, preferably between 0.05% and 5% and more preferably between 0.2% and 1% by weight. The partially hydrolysable cationic non-covalently bonded surface coating is preferably provided by an actually partially hydrolyzed cationic polymer, which preferably is hydrolyzed in the range of 40%-80%, more preferably in the range of 40%-60%, and most preferably in the range of 40%-50%. Excellent examples of such polymers are nitrogen containing polymer, which contains from 5 to 17 mol of cationic groups per kilogram of the nitrogen containing polymer. In a particular embodiment of the present invention is the coating is a partially hydrolyzed polymer of N-vinyl-alkyl-amide or N-vinyl-alkyl-imide, more preferably a polymer of N-vinyl-form-amide Finally the super absorbent gelling material is present in the absorbent cores of the present invention in a concentration of 60% by weight or more, preferably in a concentration of 80% by weight or more, more preferably in a concentration of 96% by weight or more.

For selection of the SAP material for use in the present invention it is preferable if the SAP particles have a specific surface area of at least $0.05 \text{ m}^2$ per gram, preferably $0.1 \text{ m}^2$ per gram, and more preferable more than $0.25 \text{ m}^2$ per gram in accordance with the specific surface evaluation method as defined e.g., in "Modern Super Absorbent Technology" by F. L. Buchholz and A. T. Graham, published by Wiley VCH, New York, 1998. This relative surface is an indication of the average particle size, as smaller particles will inherently result in more surface area. In this context particularly preferred embodiments of the absorbent core according to the present invention will use at least 90% by weight, preferably at least 95% by weight, more preferably 99% by weight of the SAP particles having a sieve particle size of less than 600, preferably less than 500, more preferably less than 400, micrometer, in accordance with the sieve particle size test as defined herein.

It further has been found preferable to select the SAPs used in the cores according to the present invention which have a capillary pressure percentile, in accordance with the capillary pressure evaluation method as defined herein, of at least 35, preferably at least 45, and more preferably at least 54.

DETAILED DESCRIPTION OF THE INVENTION

A. Definitions

As used herein, the term "absorbent core" refers to a component of an absorbent article that is primarily responsible for fluid handling properties of the article, including acquiring, transporting, distributing and storing body fluids. As such, the absorbent core typically does not include the topsheet or backsheet of the absorbent article.

As used herein, the term "absorbent member" refers to the components of the absorbent core that typically provide one or more fluid handling properties, e.g., fluid acquisition, fluid distribution, fluid transportation, fluid storage, etc. The absorbent member can comprise the entire absorbent core or only a portion of the absorbent core, i.e., the absorbent core can comprise one or more absorbent members.

As used herein, the terms "region(s)" or "zone(s)" of an element refer to portions or sections of that element.

As used herein, the term "comprising" means that e.g., various components, members, steps and the like can be conjointly employed according to the present invention. Accordingly, the term "comprising" encompasses the more restrictive terms "made of" and "consisting of," these latter, more restrictive terms having their standard meaning as understood in the art.

All percentages, ratios and proportions used herein are by weight unless otherwise specified.

B. Material and Components of the Absorbent Core
  1. Hydrogel Forming Absorbent Polymers
    a. Chemical Composition The SAPs or super absorbent polymers (SAPs) useful in the present invention include a variety of water-insoluble, but water-swellable polymers capable of absorbing large quantities of fluids. Such polymers materials are generally known in the art and include all those well-known polymers used or deemed useful in the context of disposable absorbent article technology. Particularly the SAPs disclosed in EP-A-752 892 or those disclosed in a textbook entitled "Modern Super Absorbent Technology" by F. L. Buchholz and A. T. Graham, published by Wiley VCH, New York, 1998 are useful in the context of the present invention.

Preferred polymer materials for use in making SAPs are slightly network cross linked polymers of partially neutralized polyacrylic acids and starch derivatives thereof. Preferably, the SAPs comprise from about 50 to about 95%, preferably about 75%, neutralized, slightly network cross linked, polyacrylic acid (i.e., poly (sodium acrylate/acrylic acid)). Network cross-linking renders the polymer substantially water-insoluble and, in part, determines the absorptive capacity and extractable polymer content characteristics of the hydrogel-forming absorbent polymers. Processes for network cross linking these polymers and typical network cross-linking agents are described in greater detail in U.S. Pat. No. 4,076,663 or references cited supra.

While the SAP is preferably of one type (i.e., homogeneous), mixtures of polymers can also be used in the present invention. The SAPs useful in the present invention can have a size, shape, and/or morphology varying over a wide range. According to the present invention these polymers are in the form of particles that do not have a large ratio of greatest dimension to smallest dimension (e.g., granules, pulverulents, inter-particle aggregates, inter-particle cross linked aggregates, and the like. The SAPs can also comprise mixtures with low levels of one or more additives, such as for example powdered silica, surfactants, glue, binders, and the like.

For particles as described above, particle size is defined as the dimension determined by sieve size analysis. The methods for determining particle sizes of the SAP particles are described in U.S. Pat. No. 5,061,259 (Goldman et. al), issued Oct. 29, 1991.

According to the present invention the SAP particles further have a substantially non-covalently bonded surface coating with a partially hydrolysable cationic polymer improving the physical characteristics of the SAP material. The covalent coating is present on the particles in an amount of less than 10% by weight of said particles, preferably between 0.05% and 5% and more preferably between 0.2% and 1% by weight. The partially hydrolysable cationic non-covalently bonded surface coating is preferably provided by an actually partially hydrolyzed cationic polymer, which preferably is hydrolyzed in the range of 40%-80%, more preferably in the range of 40%-60%, and most preferably in the range of 40%-50%.

The cationic coating preferably is a nitrogen-containing polymer (N-polymer) having 5 to 17 mol/kg (based on the weight of the nitrogen containing polymer) nitrogen atoms, which can be protonated. A detailed description of partially hydrolyzed or at least hydrolysable polyvinyl-amides and how to make them is found in DE 31,28,478. Particularly preferred are cationic coatings provided by a polymer made from a homo-polymerization of N-vinyl-form-amide, which is hydrolyzed to a degree of 30 mol % to 80 mol %. Solutions of fully or partially hydrolyzed polyvinyl-form-amides are available commercially e.g., from BASF-AG, Ludwigshafen under the trade names Basocoll™, Luredur™, or Catiofast™.

Preferably such cationic polymers have a weight-average molecular weight in the range of about 10,000 to about 500,000. Preferably the amount of the coating with N-polymer in weight % of the SAP particles is from 0.001% to 0.5%. The N-polymer can be applied to the surface cross-linked SAP particles by simple spraying of a solution comprising the N-polymer onto the particles in a mixer. Alternatively the cationic polymer, preferably the described N-Polymer can be carried onto the SAP particles by a carrier selected from cellulose and its derivatives, rayon, polypropylene, polyester, polyethylene, polyacryl, polyamide, polystyrol, polyurethane, polyacrylnitril or hydrophilic nylon, provided such carriers are incorporated into the SAP particles during polymerization or in physical form during making of the SAP particles. Of course care needs to be taken to maintain the physical properties according to the present invention as indicated below. As another alternative the N-polymer can be applied to the base particles by mixing a fine powder of the N-polymer with the particles in conventional mixing equipment. It is even possible to introduce the N-polymer into absorbent structures already comprising base particles. The N-polymer is transferred from materials in the vicinity of the particles. In absorbent cores the N-polymer can e.g., be imported into the core by impregnation onto tissues or nonwoven or polymeric film or other substrates.

Other compounds usual in the art, such as salts for pH buffering or neutralization and dust reducing compounds, or other reaction and process aids can be used in the conventional manner.

b. Physical Properties (1). Porosity of Hydrogel Layer

An important characteristic of SAPs, which is preferably achieved by the SAPs according to the present invention, is the openness or porosity of the hydrogel zone or layer formed when the polymer is swollen in body fluids under a confining pressure. This is referred to as PHL as defined supra. Preferred SAPs useful in the present invention have PHL values of at least about 0.15, preferably at least about 0.18, more preferably at least about 0.20 and most preferably at least about 0.25. Typically, these PHL values are in the range of from about 0.15 to about 0.40, and more typically from about 0.18 to 0.25. A method for determining the PHL value of these SAPs is provided in EP-A-752 892. The PHL value is measured in accordance with EP 752 892 at a confining pressure of 2068 Pa (0.3 psi). However the porosity remains an important aspect over the whole usage range of pressures experienced by absorbent cores, i.e., starting from no pressure to pressures such as 10 000 Pa.

(2). Performance Under Pressure (PUP)

Another important characteristic of SAPs, which is also preferably achieved by the SAPs according to the present invention, is their demand absorbency capacity under a high confining pressure. This demand-absorbency capacity is defined in EP-A-752 892 as a performance under pressure capacity (PUP capacity). The PUP capacity of preferred SAPs useful in the present invention is generally at least about 19 g/g, preferably at least about 21 g/g, more preferably at least about 23 g/g and most preferably at least about 29 g/g.

(3). Saline Flow Conductivity (SFC)

An important characteristic and mandatory for the SAPs useful in the present invention is their permeability or flow conductivity when swollen with body fluids so as to form a hydrogel zone or layer. This permeability or flow conductivity is defined herein in terms of the Saline Flow Conductivity (SFC) value of the SAP. SFC measures the ability of a formed hydrogel layer to transport or distribute body fluids under usage pressures. The method for determining a SFC value is provided in EP-A-752 892. The SFC value of the SAPs useful in the present invention has already been mentioned in terms of units. As expressed herein the numerical value of a unit is $10^{-7}$ cm$^3$sec/g (or cm$^3$sec/g/10,000,000). In other words 30 SFC units means an SFU value of 30 times $10^{-7}$ cm3sec/g.

(4). Extractable Polymer

Another important characteristic of particularly preferred SAPs useful in the present invention is the level of extractable polymer material present therein. Evaluation and explanation of which levels of extractable polymer is still acceptable is disclosed and explained in detail in EP-A-752 892. As a general rule the extractable amount should be as low as possible and the lower it is the less undesired reaction the extractable material can cause.

(5). Gel Volume

Another characteristic that can be important especially for preferred embodiments of SAPs useful in the present invention is gel volume. Evaluation and explanation of quality and quantity of gel volume characteristic is disclosed and explained in detail in EP-A-752 892. Preferred SAPs have a relatively high gel volume of at least about 20 g/g, and preferably from about 25 to about 80 g/g.

(6). Gel Strength

Another characteristic that can be important for preferred SAPs useful in the present invention is gel strength. As used herein, "gel strength" relates to the tendency of the SAP particles formed from the absorbent polymer to deform or "flow" under usage stresses. The gel strength measurement of SAPs is disclosed in EP-A-752 892. Although maximizing gel strength is not as critical as some other properties preferred SAPs of the present invention have a relatively high gel strength of at least about 5 kPa (10,000 dynes/cm2), more preferably at least about 10 kPa (20,000 dynes/cm2) or even above about 20 kPa (40,000 dynes/cm2).

(7). Ball Burst Strength (BBS)

Ball burst strength is a numerical measurement for evaluation of the integrity of a SAP particle layer in a swollen state, or in other words the ability to withstand tension and torsion forces, which are occurring when using absorbent articles compromising cores according to the present invention. Thereby a prediction of the behavior of absorbent cores comprising such SAP in a high concentration can be made. In particular if the BBS is measured over time the reduction or increase of the value is a good indication of the change of wet integrity of a layer of SAP particles, which can be considered a simulation of a 100% concentration of SAP. The test methodology of BBS is disclosed in detail in U.S. Pat. No. 6,121, 509. According to the present invention the BBS value is taken after 30 minutes of swelling and after 16 hours of swelling. It has been found that in use 30 minutes is the optimum amount of time to achieve an acceptable level of core integrity.

The difference between the 30 minutes value and the 16-hour value can be expressed as a percentile fraction of the 30 minutes value thereby providing an indication of the expected change (increase or decrease) of wet integrity of the absorbent core. There are 2 aspects to be considered: the integrity of the absorbent core must be acceptable during initial use. This is a fundamental requirement. However even after initial wetting the integrity (now called wet-integrity) must remain acceptable. This is measured by the BBS after 30 minutes. Provided this is acceptable the integrity of the absorbent core has to remain acceptable for the whole usage period. Considering the longest time an absorbent article may be left on a user the integrity after 16 hours can be measured. If the resistance to external forces after such an extended time remains acceptable, i.e., there is no significant reduction of the BBS value after 16 hours relative to the 30 minute BBS value, then the SAP material used inn a core provides a high degree of wet integrity to such absorbent cores.

Some SAPs experience an increase the BBS after 16 hours relative to the 30 minute BBS value. This is then an indication of an increasing wet integrity. However both for the 30 minutes and for the 16 hour BBS a fine balance needs to found to ensure that integrity is initially achieved, is maintained and the absolute integrity is neither too low (danger of disintegration) nor too high (danger of macroscopically breaking up due to usage force exposure).

(8). Centrifuge Retention Capacity (CRC)

For most hydrogel-forming absorbent polymers, gel volume as a measurement of absorbent capacity is determined by the method described in U.S. Reissue Pat. 32,649 (Brandt et al), reissued Apr. 19, 1988 but using 0.9% saline solution instead of synthetic urine. The gel volume as well as the CRC capacity is calculated on a dry-weight basis. An alternative method for measuring gel volume can be used for SAPs that adsorb Blue Dextran (see gel volume method in Re 32,649) to the surfaces of the formed hydrogel (e.g., polymers prepared from cationic monomers). For these hydrogel-forming polymers, the Absorptive Capacity test is used, but the dry weight of the hydrogel-forming polymer is used in the calculation instead of the as-is weight. See e.g., U.S. Pat. No. 5,124,188 (Roe et al), issued Jun. 23, 1992 at Columns 27-28 for description of the Absorptive Capacity test.

For the evaluation of the centrifuge retention capacity it has been found that the so-called tea-bag-evaluation or measurement (hereinafter CRC measurement) is most appropriate to reflect the maintenance of capillary pressure at situations approaching saturation of the absorbent capability of a SAP material. For the test standard laboratory conditions (21-23° C., 50% relative humidity) are used. Sample SAP material is kept dry in a tightly closing flask or other container, which is only opened upon start of the evaluation. Other material used in the evaluation (tissues, equipment, etc.) is conditioned for 24 hours prior to measurements at the above laboratory conditions.

For the CRC measurement 0.2+/−0.0050 g of SAP particles are put into a tea bag (the bag needs to be freely liquid pervious and must retain the particles, i.e., the tea bag pores need to be not larger than the smallest particles. The tea bag should have a size of 60 mm×85 mm and is sealed by welding after filling. The tea bag is then immersed for 30 minutes in a 0.9% saline solution such that there is at least 0.83 l of solution per gram of SAP; preferably there is a substantial excess of this ratio. After the 30 minute immersion the tea bag is centrifuged at 250 g for 3 minutes to remove excess saline solution. The bag is weight to the nearest 0.01 g and the absorbed liquid is calculated. The result is reported by using the amount of dry SAP, which was put into the tea bag, as grams absorbed per gram of SAP particles.

(9). Capillary Pressure Percentile

Capillary Pressure Percentile (hereinafter referred to as CPP) is a physical characteristic of SAPs providing an indication how well the material is capable to imitate the capability of fibrous material compositions to transport liquid at various levels of saturation by capillary action. Accordingly the empirically derived CPP value provides an indication for the material characteristic to perform the task of capillary liquid transport even under wet conditions.

The CPP value is calculated from so-called fixed height absorption measurements (hereinafter referred to as FHA measurements). FHA measurements are essentially the same as the PUP but made against a gravimetric height, i.e., the liquid is absorbed by pulling it against gravity. As CRC and PUP, FHA are given in units of g/g (gram absorbed/gram material). For the calculation of CPP these FHA measurements are expressed in percent of the CRC capacity of the SAP material (since the CRC values are considered to represent the absorbent capacity limit of the SAP) and referred to as FHA %. FHA as well as these FHA % need to be identified by reference to the respective hydrostatic pressure, which has been overcome (meaning that FHA/FHA % values always require that the measuring pressure is indicated). The CPP value is the numerical average of the FHA % measurement at a pressure of two, three, and five kilopascal (equating 20 cm, 30 cm, 50 cm of?) and can be expressed by the empirically derived summation formula below.

$$CPP=[FHA\%(2\,kPa)+FHA\%(3\,kPa)+FHA\%(5\,kPa)]/3$$

The fixed height absorption method evaluates the capillary pressure of a loaded SAP bed, i.e., the ability of a bed of SAP particles to draw fluid in against a hydrostatic pressure. SAP absorbs fluid in two ways, first in incorporating the fluid in its structure (swelling) driven by osmotic forces, second the SAP forms a gel bed with interstitial capillaries, which are also filled and which achieve the transport of fluid to SAP particles not in direct contact to the fluid interface. If an SAP gel bed, loaded near to its theoretical capacity, can still exert high capillary pressure, then the SAP is used to its optimum extend, i.e., no SAP is wasted. The measurement essentially measures the amount of fluid absorbed by a sample which liquid is pulled against gravity over a fixed height.

The equipment used in the FHA method consists of the following:

a fluid reservoir with a "Mariotte-Tube" to define the 0 height fluid level $H_o$ independent of fluid consumption during measurement;

a valve in a connecting tube between fluid reservoir and the bottom of a funnel with a glass-frit, the glass frit having a pore size 4 (i.e., 4-5.5 microns), where the glass frit is positioned so that the upper frit surface defines the measurement height Hm;

a sample holder assembly comprising a cylinder made of Plexiglas with an inner diameter of 6 cm. A disc of 5.9 cm diameter for placement onto the SAP sample, which disc fits without friction into the cylinder and a weight, which has a slightly smaller diameter than the disc and provides together with the disc a pressure of 2068 PA (0.3 psi) onto the sample.

When combined the SAP is capable to acquire liquid from the frit and swell in height against a confining pressure of 2068 PA (0.3 psi). The glass materials can be obtained in any usual chemical supply store, e.g., from VWR International GmbH, Vertriebszentrum Frankfurt Insterburgerstrasse 9, D-60487 Frankfurt/M., Germany. The Plexiglas equipment and weight can be made by any skilled model work shop, e.g., Acryl & Modellbau, Peter Lorenz, Ruppertshainer Str. 14, D-65779 Kelkheim/Fischbach, Germany. In case Plexiglas is available or no model workshop can be found similar equipment can also be made from glass or stainless steal. All fittings, seals, and auxiliary laboratory equipment necessary need to be selected from equipment useful under good laboratory practices and the accuracy necessary for chemical laboratory evaluations.

It is further necessary to have a scale capable to measure up to $1/1000$ g for measuring the SAP and the amount of fluid acquired. Also for conducting the test it is necessary to put a layer of tissue between the glass frit surface and the actual SAP sample to prevent particles from entering the glass frit void spaces. The tissue is preferably a high wet strength tissue, cut to squares of 65 mm. The tissue needs to be thin and a 22.5 g/m² is useful. Such tissues are available from Frippa, Miltenberg, Germany, as HWS 22.5 g/m² (gram per square meter) tissue or can be obtained from P&G, c/o R&D-STC, attention Mr. Bruno Ehrnsperger.

For the test standard laboratory conditions (21-23° C., 50% relative humidity) are used. Sample SAP material is kept dry in a tightly closing flask or other container, which is only opened upon start of the evaluation. Other material used in the evaluation (tissues, equipment etc.) is conditioned for 24 hours prior to measurements at the above laboratory conditions. For the test measurements 0.9 g SAP is weighted to the nearest $1/100$ g, for each height at least 3 samples need to be measured. The test liquid is 0.9% saline solution. The tissue is cut and placed on the frit surface; wrinkles in the tissue are not tolerated. The sample holder is placed on the tissue and the SAP is evenly distributed. The frit is placed at the desired measurement height Hm, which is 20 cm, 30 cm or 50 cm above the height of the meniscus at the bottom of the Mariotte tube. The valve is opened to allow liquid contact and the duration of the exposure to liquid is 60 minutes, to allow substantial saturation. At the end of this time the additional weight of the wet sample is measured as the amount of absorbed saline solution (this can be done by weighing the whole sample holder assembly initially and after the test, subtracting these numbers). The weight measurements are noted down to the nearest $1/100$ g.

The result is reported for each height as percent of the absorbed saline solution according the above and the CRC absorption values. Statistical analysis is used when averaging the results to ensure the final values are accurate to a 90% (preferably 95%) confidence interval. The FHA % values are then used for calculating the CPP based on the formula given supra.

c. Methods for Making SAP

The basic SAP can be formed in any conventional manner known in the art as discussed above. Typical and preferred processes for producing these polymers are described in a long list of literature including many patent application documents and in particular the textbook "Modern Super Absorbent Technology" by F. L. Buchholz and A. T. Graham, supra, U.S. Reissue Pat. 32,649, U.S. Pat. Nos. 4,666,983, 4,625, 001, 4,625,001 4,340,706, 4,506,052 4,735,987 4,541,871, PCT application WO92/16565, PCT application WO90/08789, PCT application WO93/05080; U.S. Pat. Nos. 4,824, 901; 4,789,861, 4,587,30, 4,734,478; 5,164,459; German patent application 4,020,780 (Dahmen), and published European patent application 509,708.

Preferred methods for forming the basic SAP are those involving aqueous solution polymerization methods. The aqueous reaction mixture of monomers is subjected to polymerization conditions, which are sufficient to produce in the mixture, substantially water-insoluble, slightly network cross-linked polymer. The mass of polymer formed can then be pulverized or chopped to form individual particles.

After manufacturing of the SAP particles surface cross-linking can be used to obtain SAPs having relatively high PHL, PUP capacity and SFC values. Without being bound by theory, it is believed that surface cross-linking increases the resistance to deformation of SAP surfaces, thus reducing the degree of contact between neighboring polymer surfaces when the resultant hydrogel is deformed under an external pressure. Examples of such processes are disclosed in the references cited above.

Finally the SAP particles with the desired degree of surface cross-linking are coated (but not covalently bonded) with the cationic polymers according to the present invention. The cationic polymer, preferably a N-polymer, can be applied to the surface cross-linked SAP particles by simple spraying of a solution comprising the N-polymer onto the particles in a mixer. Alternatively the cationic polymer, preferably the described N-Polymer can be carried onto the SAP particles by a carrier selected from cellulose and its derivatives, rayon, polypropylene, polyester, polyethylene, polyacryl, polyamide, polystyrol, polyurethane, polyacrylnitril or hydrophilic nylon, provided such carriers are incorporated into the SAP particles during polymerization or in physical form during making of the SAP particles. As another alternative especially the N-polymer can be applied to the base particles by mixing a fine powder of the N-polymer with the particles in conventional mixing equipment. It is even possible to introduce the N-polymer into absorbent structures already comprising base particles. The N-polymer is transferred from materials in the vicinity of the particles. In absorbent cores the N-polymer can e.g., be imported into the core by impregnation onto tissues or non-woven or polymeric film or other substrates. Of course care needs to be taken to maintain the physical properties according to the present invention as indicated herein.

When applying the cationic polymer (preferably the N-polymer) to the SAP particles it is important not to bind the coating material covalently to the surface of the SAP particles. It has surprisingly been found, that upon application of the preferred N-polymers according to the present invention, it is neither necessary nor advantageous to bind the cationic polymer to the base particles. To ensure this temperature and duration of the mixing step are critical characteristics to obtain a coating without bonding, which is sufficiently strong on one hand but effective enough to allow maintaining the wet integrity of absorbent cores made with this SAP.

C. Absorbent Cores Containing SAPs

According to the present invention absorbent cores for disposable absorbent articles comprise the previously described SAPs, with or without other optional components such as fibers, thermoplastic material, foams, scrims etc. These absorbent cores function as fluid storage members. The principle function of such cores is to absorb the discharged body fluid either directly or from other absorbent members (e.g., fluid acquisition/distribution members), and then retain such fluid, even when subjected to pressures and tensions and torsions normally encountered as a result of the wearer's movements of absorbent articles made therewith. It should be understood, however, that such polymer-containing absorbent members can also serve functions other than fluid storage.

An important aspect of these absorbent members according to the present invention is that they contain one or more regions having a high concentration of these SAPs in order to provide relatively thin absorbent articles capable of absorbing and retaining large quantities of body fluids. A high concentration of SAPs, in accordance with the present invention, is desirable to reduce the level of other components, in particular fibrous components.

In measuring the concentration of SAP in a given region of an absorbent core, the percent by weight of the SAP relative to the combined weight of SAP and any other components (e.g., fibers, thermoplastic material, etc.) that are present in the same region containing the polymer is used. With this in mind, the concentration of the SAPs in a given region of an absorbent member according to the present invention can be in the range of from about 60 to 100%, preferably from about 70 to 100%, more preferably from about 80 to 100%, and most preferably from about 90% to 100%.

Absorbent cores according to the present invention comprising high concentrations of SAPs are useful alone or in combination with other absorbent members as part of the absorbent articles according to the present invention. Depending on the intended use, the preferred cores according the present invention comprise the SAPs according to the present invention in a basis weight of at least 50 $g/m^2$, preferably at least 150 $g/m^2$ and even more preferably of at least 300 $g/m^2$.

These other absorbent members in the cores according to the present invention can include those useful for initially acquiring the discharged body fluids before these fluids are distributed to the fluid storage member of the absorbent core. These include absorbent members that provide multiple fluid handling properties (e.g., fluid acquisition and distribution) or single fluid handling properties (e.g., fluid distribution). These other absorbent members can also comprise lower concentrations of the SAPs that have the physical properties previously specified or can comprise SAPs having different physical properties.

One suitable absorbent core according to the present invention comprises an assembly having (a) an acquisition layer substantially free of SAPs; and (b) an optional SAP layer mainly comprising a first SAP that does not need to satisfy the above physical criteria and (c) another optional layer having void space for storage and redistribution of body fluids and (d) a lower layer that contains a high concentration of a second SAP that does satisfy the above physical criteria. This assembly or parts thereof may in addition be fully or partially wrapped in a tissue or other substrate in order to unitize the assembly.

D. Absorbent Articles

Because of the unique absorbent properties of the absorbent cores of the present invention, they are especially suitable for use in disposable absorbent articles for absorption of urine (also referred to as disposable absorbent incontinence articles). These absorbent articles typically comprise a liquid impervious (but preferably gas pervious) backsheet, a fluid pervious topsheet joined to, or otherwise associated with the backsheet, and the absorbent core according to the present invention positioned between the backsheet and the topsheet. Such articles are well known in the art and fully disclosed in various documents mentioned throughout the description e.g., in EP 752 892.

Examples of SAP according to the present invention for use in absorbent cores according to the present invention.

1. Preparation of a Surface Cross-Linked Base Polymer

A base polymeric gel material is prepared in a conventional manner from acrylic acid, sodium acrylat and ethoxilated trimetylo-propane-triacrylat having a centrifuge retention capacity (CRC) of 30-31 g/g and a acrylic acid neutralization of 70 mol-%. The polymeric gel material is mechanically crushed and dried in a conventional laboratory drier. After drying the polymer is ground to particles and sieved to retain the particle fraction between 150 micrometer and 850 micrometer. These particles are then surface cross linked by introducing them into a laboratory powder mixer, into which an aqueous surface cross-linking solution (0.08% oxazolidinon, 0.02% sorbitan-monolaureat and 3.5% 1,2-propandiol, each % based on the weight of the polymer particles) was sprayed with a dual phase nozzle. Thereafter 0.5% (by weight of the particles) of an aluminum sulfate (provided as 26.8% aqueous solution) was also sprayed into the powder mixer, and tempered for about 80 minutes at 175-180° C. The surface cross-linked polymer particles were then allowed to cool to ambient temperature and sieved to a particle fraction between 150-micrometer and to 850-micrometer particle range to remove particle clogs. Characteristics in accordance with the present invention of this base surface cross-linked polymer are included in Table 2 for reference.

2. Non-Covalently Bonded Surface Coating with a Partially Hydrolysable Cationic Polymer 1200 g of the base surface cross-linked polymer particles are put into a 5-liter Loedige-plough-laboratory mixer at ambient temperature. At a rotation speed of 200 rpm the surface coating of a partially hydrolysable cationic polymer was added over 13 minutes by spraying through a dual-phase nozzle using nitrogen as inert mixing gas at a pressure of about 1 bar. For the coating with partially hydrolysable cationic polymer 5 different polyvinyl amines were used, differing by various degrees of hydrolyzation as can be seen from Table 1. The polyvinyl-amine was provided as a 7.3% by weight solution at an amount of 65.71 g. This solution was pumped for even distribution through the dual-phase nozzle for spraying onto the particles in the mixer. The resulting material was afterwards transferred into an analog preheated Loedige-plough-laboratory mixer and dried at a temperature of 100° C. for 60 minutes at a mixer speed of 50 rpm. The amount of the polyvinyl-amine polymer was such that it represented 0.4% by weight of the polymer particles.

TABLE 1

| | Example | | | | |
|---|---|---|---|---|---|
| | 1 | 2 | 3 | 4 | 5 |
| Degree of hydro-lysation [mol %] | 95% | 75% | 44% | 31% | 14% |
| Commercial Identification name of BASF for this polyvinyl amine solution | Bosocoll PR 8086 | Bosocoll PR 8092 | Luredor PR 8097 | Bosocoll PR 8095 | Bosocoll PR 8094 |

The molecular weight in all examples was about 400,000 Dalton

TABLE 2

| Example | DoH mol % | PNA mol/kg | SFC cm$^3$sec/g | BBS (30-minutes) gf | BBS (16-hours) gf | BBS reduct. % | CRC g/g |
|---|---|---|---|---|---|---|---|
| *Base polymer | — | — | 111 | <10 | <10 | — | 27.5 |
| 1 | 95 | 21.4 | 133 | 169 | 160 | 5 | 27.1 |
| 2 | 75 | 15.0 | 138 | 196 | 150 | 23 | 26.9 |
| 3 | 44 | 7.5 | 229 | 169 | 110 | 35 | 27.3 |
| *4 | 31 | 5.0 | 104 | 55 | 27 | 51 | 26.9 |
| *5 | 14 | 2.1 | 111 | 21 | — | — | 26.9 |

Abbreviations/indications:
DoH = Degree of Hydrolisation;
PNA = Protonatable Nitrogen Atoms,
gf = grams of force,
*outside the present invention As can be seen from the examples the SAP of example 3 is best in class as it provides exceptionally high saline flow conductivity (indicative of its capability to provide even under wet conditions, i.e., after initial or repeated absorption, good conductivity of liquid) and a low BBS reduction (indicative that the integrity of absorbent cores with this SAP will be maintained reasonably close to the integrity of the dry absorbent core). Such beneficial performance is not achievable without the coating according to the present invention.

Parallel with the present specification a detailed description of the making and evaluating processes used for making SAP particles according to the present invention is filed in a patent application entitled "Wasserabsorbierendes Mittel und Verfahren zu seiner Herstellung" by applicant/assignee BASF, Ludwigshafen of Germany. A copy of this application is available in the file of the European patent office of the present application.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising an absorbent core, the absorbent core comprising:
   a. a super absorbent polymer, the super absorbent polymer being in the form of particles; and
   b. a nitrogenous polymer comprising from 5 to 17 mol/kg, based on the total weight of the nitrogenous polymer, of protonatable nitrogen atoms.

2. The disposable absorbent article of claim 1, wherein the particles are surface cross-linked.

3. The disposable absorbent article of claim 1, wherein the particles are surface coated with the nitrogenous polymer.

4. The disposable absorbent article of claim 3, wherein the nitrogenous polymer is non-covalently bonded to the particle.

5. The disposable absorbent article of claim 1, wherein the nitrogenous polymer is a partially hydrolyzed cationic polymer.

6. The disposable absorbent article of claim 5, wherein the nitrogenous polymer is hydrolyzed in the range of from about 40% to 80%.

7. The disposable absorbent article of claim 5, wherein the nitrogenous polymer is hydrolyzed in the range of from about 40% to 60%.

8. The disposable absorbent article of claim 5, wherein the nitrogenous polymer is hydrolyzed in the range of from about 40% to 50%.

9. The disposable absorbent article of claim 1, wherein the nitrogenous polymer is a partially hydrolyzed polymer of N-vinyl-alkyl-amide, a partially hydrolyzed polymer of N-vinyl-alkyl-imide, or a polymer of N-vinyl-form-amide.

10. The disposable absorbent article of claim 1, wherein the nitrogenous polymer is present in an amount of between about 0.05% and 5% by weight of the particles.

11. The disposable absorbent article of claim 1, wherein the nitrogenous polymer is present in an amount of between about 0.2% and 1% by weight of the particles.

12. The disposable absorbent article of claim 1, wherein the super absorbent polymer is present in the core in a concentration of at least about 80% by weight of the core.

13. The disposable absorbent article of claim 1, wherein the super absorbent polymer is present in the core in a concentration of at least about 96% by weight of the core.

14. The disposable absorbent article of claim 1, wherein the particles have a specific surface area of at least about 0.05 $m^2$ per gram.

15. The disposable absorbent article of claim 1, wherein the particles have a capillary pressure percentile, in accordance with the capillary pressure evaluation method as defined herein, of at least about 35.

16. The disposable absorbent article of claim 15, wherein the particles have a capillary pressure percentile, in accordance with the capillary pressure evaluation method as defined herein, of at least about 45.

17. The disposable absorbent article of claim 15, wherein the particles have a capillary pressure percentile, in accordance with the capillary pressure evaluation method as defined herein, of at least about 54.

18. The disposable absorbent article of claim 17, further comprising a topsheet positioned adjacent the absorbent core.

* * * * *